(12) United States Patent
Metz et al.

(10) Patent No.: US 6,569,403 B1
(45) Date of Patent: *May 27, 2003

(54) DETERMINING EFFECTS OF EXTERNAL STIMULI ON THE BRAIN USING PET

(75) Inventors: John T. Metz, Chicago, IL (US); Malcolm D. Cooper, Chicago, IL (US)

(73) Assignee: Miicro, Incorporated, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/551,330

(22) Filed: Apr. 18, 2000

Related U.S. Application Data

(63) Continuation of application No. 09/178,993, filed on Oct. 26, 1998, now Pat. No. 6,051,209, which is a continuation-in-part of application No. 08/522,685, filed on Sep. 1, 1995, now Pat. No. 5,827,499.

(51) Int. Cl.⁷ .................. A61K 49/00; A61K 51/00; G01N 31/00; G01N 33/48

(52) U.S. Cl. .................. 424/9.4; 424/9.1; 424/9.2; 424/1.73

(58) Field of Search .................. 424/9.4, 9.1, 9.2, 424/1.73

(56) References Cited

U.S. PATENT DOCUMENTS

| | | | |
|---|---|---|---|
| 4,166,452 A | 9/1979 | Generales, Jr. | 128/741 |
| 4,862,359 A | 8/1989 | Trivedi et al. | 364/413.05 |
| 5,027,817 A | 7/1991 | John | |
| 5,304,367 A | 4/1994 | Biegon | 424/1.11 |
| 5,331,969 A | 7/1994 | Silberstein | 128/731 |
| 5,827,499 A | 10/1998 | Metz et al. | 424/1.73 |
| 6,051,209 A | 4/2000 | Metz et al. | |

OTHER PUBLICATIONS

Baxter, L.R., Jr., Schwartz, J.M., Bergman, K.S., Szuba, M.P., Guze, B.H., Mazziotta, J.C., Alazraki, A., Selin, C.E., Ferng, H.–K., Munford, P. & Phelps, M.E. (1992) "Caudate Glucose Metabolic Rate Changes With Both Drug and Behavior Therapy for Obsessive–Compulsive Disorder" *Archives of General Psychiatry* 49: 681–689.

Blamire, A.M., Ogawa, S., Ugurbil, K., Rothman, D., McCarthy, G., Ellermann, J.M., Hyder, F., Rattner, Z. & Shulman, R.G. (1992) "Dynamic Mapping of the Human Visual Cortex by High–Speed Magnetic Resonance Imaging" *Proceedings of the National Academy of Sciences USA* 89: 11069–11073.

Blin, J., Ivaniu, A., De Volder, A., Michel, C., Bol, A., Verellen, C., Seron, X., Duprez, T. & Laterre, E.C. (1998) "Physostigmine Results in an Increased Decrement in Brain Glucose Consumption in Alzheimer's Disease" *Psychopharmacology* 136: 256–263.

Buchsbaum, M.S., Potkin, S.G., Siegel, B.V., Jr., Lohr, J., Katz, M., Gottschalk, L.A., Gulasekaram, B., Marshall, J.F., Lottenberg, S., Teng, C.Y., Abel, L., Plon, L. & Bunney, W.E., Jr. (1992) "Striatal Metabolic Rate and Clinical Response to Neuroleptics in Schizophrenia" *Archives of General Psychiatry* 49: 966–974.

Buchsbaum, M.S., Siegel, B.V., Jr., Wu, J.C., Hazlett, E., Sicotte, N. & Haier, R. (1992) "Brief Report: Attention Performance in Autism and Regional Brain Metabolic Rate Assessed by Positron Emission Tomography" *Journal of Autism and Developmental Disorders* 22 (1): 115–125.

Buchsbaum, M.S., Potkin, S.G., Marshall, J.F., Lottenberg, S., Teng, C., Heh, C.W., Tafalla, R., Reynolds, C., Abel, L., Plon, L. & Bunney, W.E., Jr. (1992) "Effects of Clozapine and Thiothixene on Glucose Metabolic Rate in Schizophrenia" *Neuropsychopharmacology* 6 (3): 155–163.

Cook, E.H., Jr., Metz, J., Leventhal, B.L., Lebovitz, M., Nathan, M., Semerdjian, S.A., Brown, T. & Cooper, M.D. (1994) "Fluoxetine effects on cerebral glucose metabolism" *NeuroReport* 5: 1745–1748.

Cooper, M.D., Chen, C.–T., Metz, J., Polonsky, K. & Levy, J. (1991) "Effects of Insulin Mediated Plasma Glucose Changes on Brain Function" *Acta Radiologica Supplmentum* 376: 161–162.

Cooper, M., Metz, J., de Wit, H., Cook, E., Lorenz, J. & Brown, T. (1998) "Interclass Drug Effects and Changes in Regional Brain Glucose Metabolism" *Psychopharmacology Bulletin* 34 (2): 229–232.

Cooper, M. & Metz, J. (1999) "Glucose Metabolic Response to a Drug: A Biomarker for the Development of Drugs Affecting the CNS" *Biomarkers and Surrogate Endpoints: Advancing Clinical Research and Applications*, poster presentation, Natcher Conference Center, Bethesda, MD.

de Wit, H., Uhlenhuth, E.H. & Johansen, C.E. (1985) "Drug Preference in Normal Volunteers: Effects of Age and Time of Day" *Psychopharmacology* 87: 186–193.

de Wit, H., Uhlenhuth, E.H. & Johanson, C.E. (1986) "Individual Differences in the Reinforcing and Subjective Effects of Amphetamine and Diazepam" *Drug and Alcohol Dependence* 16: 341–360.

de Wit, H., Metz, J. & Cooper, M. (1989) "The Effects of 0.8 G.KG Ethanol on Cerebral Metabolism and Mood in Normal Volunteers" *NIDA Research Monographs* 95: 450.

(List continued on next page.)

Primary Examiner—William R. A. Jarvis
(74) Attorney, Agent, or Firm—McDonnell Boehnen Hulbert & Berghoff

(57) ABSTRACT

A method of evaluating the effects of administering an external stimuli or treatment such as a psychoactive compound, a drug, or an environmental influence like temperature, noise, vibration, light and similar sensory-perceived influences, on a subject's brain using imaging techniques with positron emission tomography (PET). The method measures cerebral metabolism before and after administering the external stimuli or treatment, and employs a behavioral clamp to control behavioral influences on the subject's brain after administration of the external stimuli or treatment.

6 Claims, 3 Drawing Sheets

OTHER PUBLICATIONS de Wit, H., Metz, J., Wagner, N. & Cooper, M. (1990) "Behavioral and Subjective Effects of Ethanol: Relationship to Cerebral Metabolism Using PET" *Alcoholism: Clinical and Experimental Research* 14 (3): 482–489.

de Wit, H., Metz, J., Wagner, N. & Cooper, M. (1991) "Effects of Diazepam on Cerebral Metabolism and Mood in Normal Volunteers" *Neuropsychopharmacology* 5 (1): 33–41.

de Wit, H., Metz, J. & Cooper, M. (1991) "Effects of Ethanol, Diazepam and Amphetamines on Cerebral Metabolic Rate: PET Studies Using FDG" *NIDA Research Monographs* 105: 61–67.

Evans, A.C., Marrett, S., Collins, L. & Peters, T.M. (1989) "Anatomical–Functional Correlative Analysis of the Human Brain Using Three Dimensional Imaging Systems" *Proceedings of the SPIE* 1092:264–274.

Evans, A.C., Marret, S., Torrescorzo, J., Ku, S. & Collins, L. (1991) "MRI–PET Correlation in Three Dimensions Using a Volume–of–Interest (VOI) Atlas" *Journal of Cerebral Blood Flow and Metabolism* 11: A69–A78.

Friston, K.J., Frith, C.D., Liddle, P.F. & Frackowiak, R.S.J. (1991) "Comparing Functional (PET) Images: The Assessment of Significant Change" *Journal of Cerebral Blood Flow and Metabolism* 11: 690–699.

Fox, P.T., Mintun, M.A., Reiman, E.M. & Raichle, M.E. (1988) "Enhanced Detection of Focal Brain Responses Using Intersubject Averaging and Change–Distribution Analysis of Subtracted PET Images" *Journal of Cerebral Blood Flow and Metabolism* 8: 642–653.

Fox, P.T., Raichle, M.E., Mintun, M.A. & Dence, C. (1988) "Nonoxidative Glucose Consumption During Focal Physiologic Neural Activity" *Science* 241: 462–464.

Fox, P.T. (1991) "Physiological ROI Definition by Image Subtraction" *Journal of Cerebral Blood Flow and Metabolism* 11: A79–A82.

Hazlett, E.A., Dawson, M.E., Buchsbaum, M.S. & Nuechterlein, K.H. (1993) "Reduced Regional Brain Glucose Metabolism Assessed by Positron Emission Tomography in Electrodermal Nonresponder Schizophrenics: A Pilot Study" *Journal of Abnormal Psychology* 102 (1): 39–46.

Kwong, K.K., Belliveau, J.W., Chesler, D.A., Goldberg, I.E., Weisskopf, R.M., Poncelet, B.P., Kennedy, D.N., Hoppel, B.E., Cohen, M.S., Turner, R., Cheng, H.–M., Brady, T.J. & Rosen, B.R. (1992) "Dynamic Magnetic Resonance Imaging of Human Brain Activity During Primary Sensory Stimulation" *Proceeding of the National Academy of Sciences USA* 89: 5675–5679.

Levy, D.E., Sidtis, J.J., Rottenberg, D.A., Jarden, J.O., Strother, S.C., Dhawan, V., Ginos, J.Z., Tramo, M.J., Evans, A.C. & Plum, F. (1987) "Differences in Cerebral Blood Flow and Glucose Utilization in Vegatative Versus Locked–in Patients" *Annals of Neurology* 22: 673–682.

Metz, J., Cooper, M., Brown, T., Kinnunen, L., Zajecka, J. & Cooper, D. (2000) "Quantitative Functional Imaging (FDG–PET) and Intra–Class Drug Effects" *Symposium on the Use of Imaging in Drug R&D*, poster presentation, Natcher Conference Center, Bethesda, MD.

Ogawa, S., Tank, D.W., Menon, R., Ellermann, J.M., Kim, S.–G., Merkle, H. & Ugurbil, K. (1992) "Intrinsic Signal Changes Accompanying Sensory Stimulation: Functional Brain Mapping with Magnetic Resonance Imaging" *Proceedings of the National Academy of Sciences USA* 89: 5951–5955.

Pelizzari, C.A., Chen, G.T.Y., Spelbring, D.R., Weichselbaum, R.R. & Chen, C.–T. (1989) "Accurate Three–Dimensional Registration of CT, PET, and/or MR Images of the Brain" *Journal of Computer Assisted Tomography* 13 (1): 20–26.

Phelps, M.E., Huang, S.C., Hoffman, E.J., Selin, C., Sokoloff, L. & Kuhl, D.E. (1978) "Tomographic Measurements of Local Cerebral Glucose Metabolic Rate in Humans with (F–18)2–Fluoro–2–Deoxy–D–Glucose: Validation of Method" *Annals of Neurology* 6: 371–388.

Phelps, M.E. (2000) "Positron Emission Tomography Provides Molecular Imaging of Biological Processes" *Proceedings of the National Academy of Sciences USA* 97 (16): 9226–9233.

Potkin, S.G., Buchsbaum, M.S., Jin, Y., Tang, C., Telford, J., Friedman, G., Lottenberg, S., Najafi, A., Gulasekaram, B., Costa, J., Richmond, G.H. & Bunney, W.E., Jr. (1994) "Clozapine Effects on Glucose Metabolic Rate in Striatum and Frontal Cortex" *Journal of Clinical Psychiatry* 55 (9, Suppl. B): 63–66.

Raichle, M.E. (1998) "Behind the Scenes of Functional Brain Imaging: A Historical and Physiological Perspective" *Proceedings of the National Academy of Sciences USA* 95: 765–772.

Reivich, M., Kuhl, D., Wolf, A., Greenberg, J., Phelps, M., Ido, T., Casella, V., Fowler, J., Hoffman, E., Alavi, A., Som, P. & Sokoloff, L. (1979) "The [18F]Fluorodeoxyglucose Method for the Measurement of Local Cerebral Glucose Utilization in Man" *Circulation Research* 44: 127–137.

Shulman, R.G., Rothman, D.L. & Hyder, F. (1999) "Stimulated Changes in Localized Cerebral Energy Consumption Under Anesthesia" *Proceedings of the National Academy of Sciences USA* 96: 3245–3250.

Sokoloff, L. (1985) "Basic Principles in Imaging of Regional Cerebral Metabolic Rates" in *Brain Imaging and Brain Function*, L. Sokoloff, Ed., Raven Press: New York, N.Y., pp. 21–49.

Swartz, B.E., Thomas, K., Simpkins, F., Kovalik, E. & Mandelkern, M.M. (1999) "Rapid Quantitative Analysis of Individual 18–FDG–PET Scans" *Clinical Positron Imaging* 2: 47–56.

Volkow, N.D., Hitzemann, R., Wolf, A.P., Logan, J., Fowler, J.S., Christman, D., Dewey, S.L., Schlyer, D., Burr, G., Vitkkun, S. & Hirschowitz, J. (1990) "Acute Effects of Ethanol on Regional Brain Glucose Metabolism and Transport" *Psychiatry Research: Neuroimaging* 35: 39–48

Volkow, N.D., Rosen, B. & Farde, L. (1997) "Imaging the Living Human Brain: Magnetic Resonance Imaging and Positron Emission Tomography" *Proceedings of the National Academy of Sciences USA* 94: 2787–2788.

Weng, X., Ding, Y.–S. & Volkow, N.D. (1999) "Imaging the Functioning Human Brain" *Proceeding of the National Academy of Sciences USA* 96: 11073–11074.

European Search Report for European Patent Application No. EP 99121023.8, Jan. 2001.

DETERMINING EFFECTS OF EXTERNAL STIMULI ON THE BRAIN USING PET

CROSS-REFERENCE TO RELATED APPLICATIONS

This application is a continuation of U.S. patent app. Ser. No. 09/178,993, filed Oct. 26, 1998, now U.S. Pat. No. 6,051,209, which is a continuation-in-part of U.S. patent app. Ser. No. 08/522,685, filed Sep. 1, 1995, now U.S. Pat. No. 5,827,499. All of the patent, patent applications, as well as any other scientific and technical writings referred to herein are incorporated herein by reference to the extent that they are not contradictory.

BACKGROUND OF THE INVENTION

The present invention relates to a method of evaluating the effects of external stimuli, such as pharmaceutical drugs and environmental influences like fragrances, temperature, noise, light, etc. on a subject's brain, and more particularly to a method of evaluating the effects of administering such stimuli on a subject's brain using imaging techniques with positron emission tomography (PET).

Positron emission tomography (PET) is a radiotracer based method for producing images that quantitatively represent some biochemical property of the body (or portions of the body). In relation to this work, use of PET is confined to metabolic imaging of the brain. Although other methods are often used, the aspect of PET that is relevant to this particular work involves 2-fluoro-deoxyglucose (FDG) as the tracer in studies of cerebral metabolism and oxygen-15 labeled water (0–15) as the tracer in studies of cerebral blood flow. In general, FDG is used to estimate the rate of metabolism of glucose in different parts of the brain (Sokoloff, 1985) and provides data that represent integrated metabolic activity over a 20–40 minute period. 0–15 studies determine rate of blood flow in different parts of the brain with an integration period of 40–60 seconds. Given the different temporal demands of the two kinds of tracers, metabolic studies with FDG reveal relatively long-lasting effects or conditions (such as pathologies), whereas 0–15 studies are more sensitive to rapid, transient activity (such as sensory processes or cognition).

The problem that we are interested in is to determine how certain external stimuli or treatments affect cerebral metabolism. The external stimuli or treatments are usually drugs, but other interventions would be faced with the same considerations. For example, environmental influences such as fragrances, temperature, noise, taste, vibration, light and similar stimuli clearly effect cerebral metabolism. The basic paradigm which we use to study external stimuli or treatments is conceptually very simple: 1) measure metabolism without any external stimuli or treatment; 2) apply the external stimuli or treatment; 3) measure metabolism again; and 4) determine whether the measurement at step 3 is statistically different from the measurement at step 1. In actuality, there are a number of experimental difficulties that must be dealt with before this paradigm can be applied.

First of all, it is important to realize that all images provided by PET reflect every influence on the brain at the time of a study. All perceptions, movements, thoughts, and moods, as well as vegetative functions, have correlates in brain metabolism and blood flow, and these factors, which are always present, may obscure effects due to external stimuli or treatment. Even more critically, these factors may change in unknown ways in response to the external stimuli or treatment and hence the extent of their influence on observed metabolism becomes unpredictable. It can, therefore, be difficult to determine which features of an image are due specifically to the experimental treatment and which are secondary, due to some other change that occurs because of the treatment. The objective of much of the present work has been to develop ways of processing PET images to more easily identify metabolic effects that are due to a specific external stimuli or treatment.

Some of our earliest work involved the recognition that the condition of subjects at the time of a study might vary from subject to subject or even within the same subject at different times (Levy et al., 1987). Variation in the testing condition thus could make it difficult to isolate differences introduced by an external stimuli or treatment.

Accordingly, we have developed an appropriate standard condition for testing subjects. This condition is the visual monitoring task (VMT). The VMT requires that subjects watch a screen on which is projected either a bright light or a dim light. The lights are easily distinguished from each other. One light flashes at a varying interval of 4 to 7 seconds. The two lights are equally probable. We ordinarily test subjects for 3 to 4 blocks (96 total trials each block, about 10 minutes per block) with a slight break between blocks. Subjects are instructed to press a button every time the dim light flashes and to ignore the bright flashes (a very subtle point: the natural tendency is to respond to the bright light which is more salient; by making the dim light the target a slight increase in difficulty is introduced). A computer measures reaction time (RT) to each button press (expressed as median RT per block) and whether the press was correct (a dim light), false alarm (a bright light), or missing (dim light flashed but subject did not press the button). In some situations, the VMT includes a feedback system so that subjects could see how fast their RT's to target flashes were. This produces more consistent RT's (lower variance). The VMT differs from other tasks that are occasionally used in PET studies (Buchsbaum et al., 1992; Hazlett et al., 1993) in that it is extremely simple and undemanding—subjects can do this task even if they are very young, very old, or slightly affected by a drug. At the same time, successful performance of the task precludes extraneous mental activity.

In early drug/PET work, a common procedure was to use a fairly large dose of a drug in order to produce the largest practical metabolic or blood flow "signal". We, however, immediately recognized that this would create a problem. Some of the drugs that we were planning to study (e.g., ethanol, diazepam) would likely incapacitate subjects to the point where they would not be able to perform the VMT adequately. However, we were convinced that any dramatic change in behavior as a result of taking a drug would be impossible to interpret (as an extreme example, subjects who are sleeping after a drink of ethanol should not be compared to waking subjects—there would undoubtedly be differences, but these would not be due to the drug but the condition of the subjects). Therefore, use of the VMT as part of our drug studies necessarily limits the dose of some drugs that can be studied. Thus, we chose to sacrifice a large but confounded signal in order to get a small but clean signal.

We also recognized that some subjects became very competitive while performing the VMT, visibly trying to get the lowest possible RT. We thus recognized that the demands of the VMT affected different subjects differently and perhaps would affect them differently under various drug conditions and/or other external stimuli treatments. Therefore, (and as now used in the OMEI process) we eliminated the RT feedback. Instead, we explicitly adopted an exclusion criterion: any condition on which RT is not stable (operationally defined as deviating by more than 10% from a reference condition) must be discarded. Similarly, any subject who does not perform with at least 95% accuracy (combined hits and correct rejections) must be omitted. Because subjects are confined to a relatively narrow range of behavior, we refer to this phase of the process as a "behavioral clamp."

The VMT provides fairly good control of subject's overt behavior and even of their inner behavior (thinking). However, it does nothing to control mood, another variable that could be different under reference versus external stimuli (e.g. drug treatment) conditions, but as with sleep in the behavioral domain, it would be incorrect to attribute metabolic changes to a drug. In order to minimize the contribution of mood to metabolic changes that we would observe, we introduced into the PET experiments a standard test procedure. We administer the Profile of Mood States—POMS (McNair et al., 1971), a brief self-administered adjective check list that has been shown to be sensitive to drug effects (de Wit et al., 1985; de Wit et al., 1986) and other external stimuli. POMS scale scores are determined before and after the placebo and before and after the administration of the stimuli treatment. The difference between these scores indicates how much mood changed as a result of the administration of the stimuli or treatment, as opposed to changes due to fatigue, boredom, etc. We recognize that mood is difficult to control, but by measuring it we can incorporate significant mood changes into our interpretation of metabolic changes. Where practical, this often involves separating subjects who change in mood from those who do not (or who change in the opposite direction) and creating different images of metabolic change for each group.

Having deliberately chosen to deal with relatively small signals due to our external stimuli or treatment, we were next faced with the problem of detecting those signals. The standard method of dealing with metabolic images in PET studies (prior to OMEI) consists of drawing anatomical regions of interest (ROIs) on the slices that the scanner provides; this is done under both reference and treatment conditions. In its more recent form (Gut et al., 1995a), the ROIs are drawn on each subject's PI then applied to the PET images that are spatially correlated (in three dimensions) with the MRI. In either form, this method is relatively insensitive to small changes in brain metabolism (Fox, 1991).

1. Even with the best positioning techniques, there will be slight differences in positioning of subjects on different occasions. In the case of repeated 0–15 scans we have even noticed significant changes in subject positions (up to 5 mm) within the same session; this problem, of course, is exacerbated when metabolic studies occur in different sessions on different days. This means that slices of the brain in one condition will not correspond exactly to ROIs from another condition.

2. The problem of different slices is even more serious when looking at different subjects since anatomical differences will prevent definition of identical ROIs.

3. Even the best drawing of ROIs cannot perfectly define all regions identically in all subjects. Not only will experimenter error and biases be present, but differences in anatomical features will cause some variation in definition of ROIs.

4. Any ROI must necessarily include relatively unresponsive subregions (e.g., white matter, portions near boundaries of ventricles or external surfaces that incorporate different partial volume effects).

5. True physiological effects will often not fill an entire ROI, no matter how small the ROIs may be.

6. Because the ROIs are defined independently of each other, physiological effects that cross ROI boundaries may fail to show up in any one ROI even though an effect may be relatively large.

The first five of these considerations serve to add "noise" to the signal that we would be trying to detect; the sixth effectively reduces the size of a signal even further. Nevertheless, to our knowledge all PET metabolic studies to date, including our own (de Wit et al., 1988; de Wit et al., 1991), have used this basic approach. This approach, as we and others demonstrated, can work in the sense of demonstrating robust effects. When combined with the behavioral clamp procedure, this approach can certainly provide interpretable metabolic images. At worst, it would only require the studying of a sufficiently large number of subjects to determine effects of any external stimuli (e.g. drug) treatment (this, of course, can be practically impossible, given the cost of PET studies).

Coincidentally with these metabolic studies, however, others were conducting studies of cerebral blood flow with 0–15. In these studies it was early recognized that small signals were involved and therefore more sensitive analytic approaches were required. Such approaches were developed in several laboratories (Fox et al., 1988; Fox and Mintun, 1989). Underlying these more sensitive methods were two conceptual shifts from the standard procedure.

The first as a recognition that PET was providing true physiological data, not anatomical data (Fox, 1991). It stands to reason, therefore, that the physiological data itself would be more sensitive than a priori anatomical features. In this sense, these methods were "data driven". The second shift was an effective realization that the slice-based data provided by PET scanners are estimates of true metabolic activity in the brain. Alternative ways of estimating metabolic activity can be validly employed. Briefly, the PET brain could be conceived of as a whole, relatively smooth volume rather than a set of discrete slices. Of course there are assumptions and limitations in this volumetric approach, but they are not necessarily worse than those of the slice-based approach. Most important, the volumetric approach allows for different kinds of data manipulation in experimental settings.

Specifically, estimates can be made for the metabolic value at every point in the brain and the brain can all be transformed into a standard three-dimensional space. Several different methods have been developed for estimating all points in the brain volume. Basically, they all involve interpolation from measured slice centers to every point in the vicinity of the slice center. At present, only linear interpolations have been employed but other methods are being researched (Lin et al., 1988; Lin et al., 1989). Likewise, the transformation problem has been solved several times (Evans et al., 1987; Fox et al., 1988; Evans et al., 1991). Investigators in our laboratory have been most successful in developing the procedure for spatially correlating PET and MRI or x-ray CT images (Pelizzari et al., 1989). While not essential, this step is one more way of reducing noise due to imprecision of the spacial transformations. Although we have preferred ways of treating our data, we recognize that there are a number of comparably good techniques. The critical point for the OMEI procedure is that volumetric handling of the data with transformation into standard space is an essential part of the procedure.

The present invention involves brain-behavior relationships and methods for evaluating and measuring them using imaging techniques with positron emission tomography (PET). In particular we are concerned with methods that measure quantitative changes in blood flow, metabolism and ligand localization and binding. More specifically we have been involved with elucidating the effects of external stimuli such as drugs and other psychoactive compounds with abuse potential as well as environmental influences like fragrances, temperature, vibration, taste, noise, light and other sensory-perceived influences, and cognitive challenges concerning attention and memory. We have effected a method which enables us to measure regional metabolic changes in the brain and associated mood changes as a result of administering such external stimuli, particularly from a single-dose drug challenge, in a controlled behavioral state.

The method presents a new perspective inasmuch as it reveals the end-pathway of the external stimuli's effect by the metabolic process involved. Thus, it demonstrates those regional brain areas which effect the functional changes induced by the external stimuli, particularly by the action of a drug or psychoactive compound. Further, it can characterize the metabolic changes in quantitative terms as to whether the regional metabolic change is relatively increased or decreased. This "end-effect" measure is particularly important since we have shown it is quite distinct from the site of localization of the radiolabeled drug, its ligand-binding characteristics or the neurotransmitter systems involved.

A series of studies indicate this is an effective in vivo means of characterizing the effects of external stimuli, particularly drugs, and thus can provide a new and valuable approach to drug development. Specifically, we see an application in devising effective and efficient strategies in the clinical phases of development; not least from the ability to rapidly obtain a measure of effectiveness by direct comparison with already characterized and available compounds. We believe the method can be advantageously applied in all three clinical phases of drug development—safety, efficacy and dosage. It can also be a means to determine the effects of external stimuli, such as drug combinations and examine synergy or inhibition. Our special interest is in psychoactive compounds that effect mood and behavior and their associated neuropsychiatric disorders, but as noted above the method is applicable to other types of external stimuli. However, the approach is also applicable in drugs targeted to broader range of syndromes and disorders in the brain. Similarly, we recognize the potential in determining drug side-effects including CNS changes arising from non-brain targeted pharmaceuticals.

In terms of drug development, the efficiency of the method is an outstanding attribute. Significant measures may be obtained from as few as eight subjects and comparative results provided with a matter of weeks. It is amenable to many variations in the drug testing procedure including measures of acute and chronic effects and alterations in dosage, scheduling and delivery. It will provide an important measure of drug effect since for the first time it will be possible to relate dosage and drug plasma levels to a quantitative measure of regional changes in the central nervous system. Similarly, when these measures are related to parenchymal organ function of blood biochemistry, then toxicity versus therapeutic efficacy can be quantitatively appraised.

These considerations indicate that the method can have a significant impact upon both the cost and rate at which new drugs can be developed and brought to market. Archived compounds can be efficiently re-evaluated and, perhaps most importantly, it will increase the number and type of new compounds that can be applied in the therapy of diseases affecting the brain.

The method involves (1) measuring cerebral metabolism of a subject's brain prior to and in the absence of any external treatment with a stimuli such as a psychoactive compound; (2) administering the external stimuli such as a psychoactive compound to the subject; (3) controlling behavioral influences on the subject's brain by subjecting the subject to a behavioral clamp; (4) measuring cerebral metabolism of the subject's brain after administering the external stimuli (e.g. psychoactive compound) and during the behavioral clamp; and (5) determining any differences between cerebral metabolism prior to and in the absence of administering the external stimuli (e.g. psychoactive compound) and cerebral metabolism after administering the external stimuli (e.g. psychoactive compound).

DETAILED DESCRIPTION OF THE INVENTION

Figure 1:
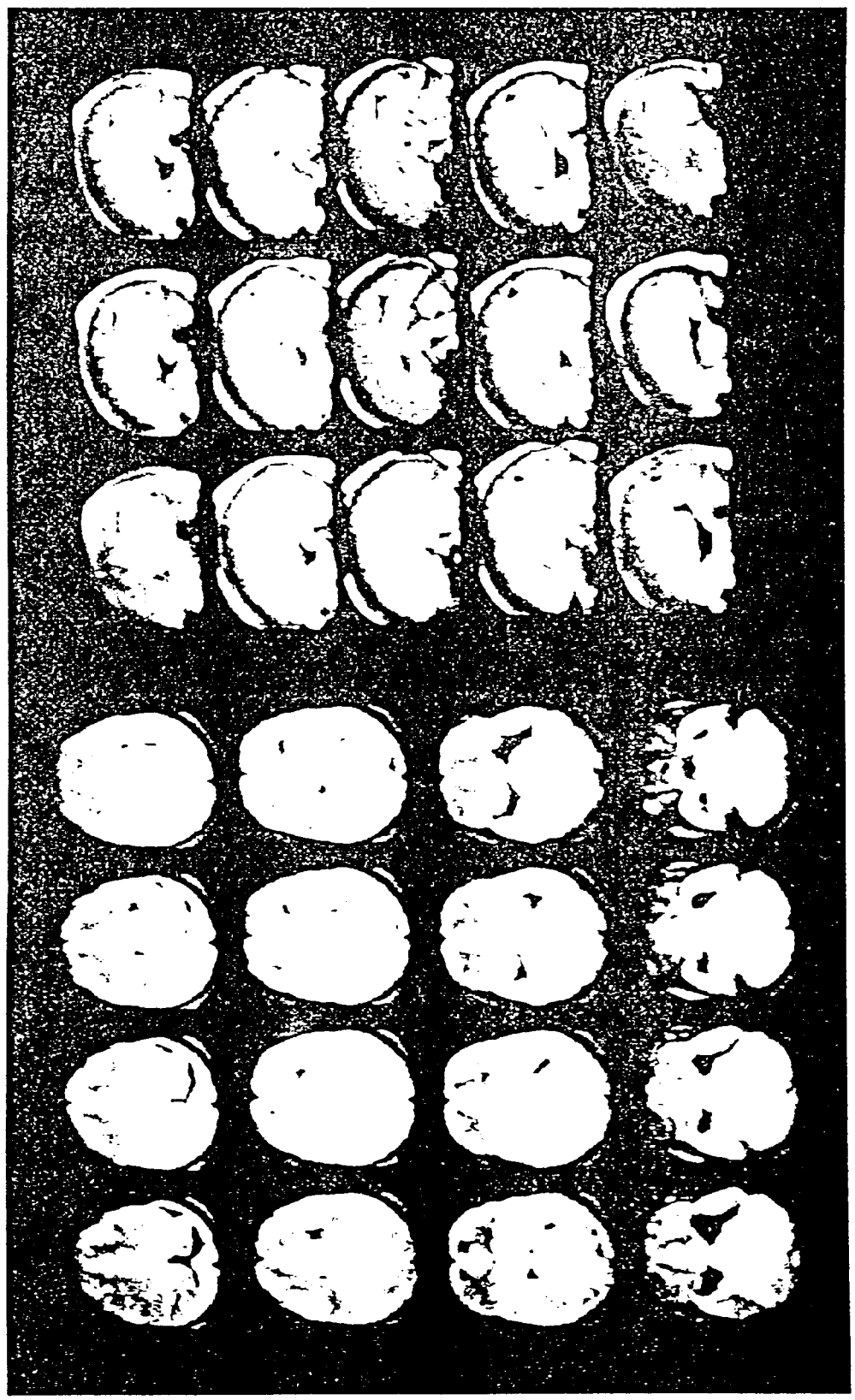
FIG. 1 illustrates a series of PET images superimposed on MRI brain images demonstrating fluoxetine effects on cerebral glucose metabolism.

The Optimization of Metabolic Effect Identification (OMEI) procedure disclosed herein uses positron emission tomograph (PET) for the purpose of identifying regions of the brain that are effected by an external stimuli or treatment. The external stimuli or treatment will usually be a pharmacological treatment but the procedure is not limited to this type of study and may be employed to determine the effects of any psychoactive compound on a patient's brain. For example pimozide, ethanol, fluoxetine, perfumes, taste or flavoring compounds, etc. are all examples of psychoactive compounds. Other environmental influences such as temperature, vibration, noise, light and other sensory-perceived influences may also be evaluated for their effects on cerebral metabolism. The procedure is effective because it reduces the influence on metabolism of effects not directly due to the treatment being studied and because it uses the most sensitive available methods for detection of areas that change in metabolism because of the treatment. Thus, the phrase "external stimuli or treatment" is intended to be any pharmaceutical drug, psychoactive compound or sensory-perceived environmental influence.

The procedure consists of four steps:

1. Collection of Metabolic Data: Two or more PET sessions are conducted for every subject. In each session, fluoro-deoxyglucose (FDG) is used as the tracer to measure regional cerebral metabolism of glucose according to standard methods (Phelps et al., 1979; Reivich et al., 1979). One of these sessions is designated as the reference session. In most cases, the reference session includes the administration of an inert treatment (placebo); the other session(s) include the administration of an external stimuli or treatment such as a drug (or drugs) which is assumed or hypothesized to affect the brain. Ideally, the treatments should be administered with a placebo in a double-blind, counterbalanced fashion at a time prior to administration of the dose of the external stimuli or treatment (within limits—see below) which permits determination of time-activity or dose-response curves. PET data can be collected in any convenient units (e.g. absolute units of glucose per unit tissue per unit time, or normalized relative to whole brain mean and standard deviation), although the ultimate interpretation will be affected by the choice of units.

2. Control of Behavioral and Subjective Influences on the Brain: In each PET session the subject performs a behavioral task which has one or more measurable variables. The behavioral task is chosen so as to maintain subjects in a standard and stable condition throughout the period of FDG equilibration (20–40 minutes after injection). The task must be capable of being performed at comparable levels by all subjects with or without the external stimuli or treatments that may be used in the study. Thus, the task should be relatively simple, requiring a non-stressful level of attention with no opportunity for developing a productive strategy. The measurable variables associated with the task are used to define criteria for a valid study: only subjects who perform the task at a specified level are included in subsequent analyses. Because subjects are behaviorally restricted to a relatively narrow range of responses, we refer to this step as a "behavioral clamp". Implicit to this approach is a recognition that only certain levels of the treatment can be studied by this method. For example, a dose of a drug which invariable produces sleep or uncontrollable agitation could not be studied. In our usual application, the clamp consists of visual monitoring task (VMT) is which the subject is asked to press a button held in one hand every time a dim light is flashed on a screen but to ignore an equally probably and easily discriminated bright flash. Bright or dim lights flash randomly for 250 msec at varying intervals between 4 and 7 seconds. Arbitrarily, we set the validity level at 95% accuracy with reaction times varying in experimental conditions by no more than ±10% from the reference condition for each subject.

The task should also minimize subjective variables such as extraneous ideation, motivation, anxiety, etc. In part, this is accomplished by the choice of a behavioral clamp which is sufficiently but not excessively demanding; this is verified by the overall stability of performance by subjects across a wide range of treatments and subjects. In addition, some subjective variables can be quantified by standard psychological instruments. We administer the Profile of Mood States (POMS) (McNair et al., 1971) before and immediately after the equilibration period. If there is a significant group difference as a function of treatment, the subjects are divided into subgroups so as to facilitate attribution of image differences to the measured subjective differences. Thus, there are two components to this step: clamping the behavior and measuring mood.

3. Transposition of Image Data into Standard Computer Space: Metabolic image data collected from each subject are transposed into a standard anatomical space. This involves shifting, shrinking or expanding, and rotating PET image sets so that any point within the image-brain of one subject corresponds (in x, y, and z coordinates) to the same point in the image-brain of that subject under different conditions and to the same point in the image-brains of all other subjects. Several methods could be used to achieve this. We use a set of standard anatomical landmarks which can be identified in each three dimensional image-brain. The landmarks are then adjusted to correspond to their location in the Talairach atlas (Talairach and Tournoux, 1988). This process is facilitated by the collection of anatomical image-brain with the metabolic image-brain in computer space. We use the method of Pelazzari and colleagues, which was developed in our laboratory (Pelizzari et al., 1989); other methods could also be used. The landmarks are then identified in the anatomical image-brain, applied to the metabolic image-brain, and transformed into the Talairach space.

4. Detection of Areas of Treatment Effects: A number of methods can be used to distinguish areas of the brain that show marked differences between the treatment conditions. We use a modification of statistical parametric mapping (Friston et al., 1991) in which within-subject t-tests are performed at each voxel in the standardized image-brains for each stimulated condition compared to the reference condition. The level for reporting differences is set depending on the requirements of the study. Simpler analyses, such as subtractions of the treatment mean images from the reference mean image can be used for preliminary analyses.

We claim a unique contribution especially for the development of step 2. The other steps are widely employed and accepted in the PET literature. We also claim the first recognition of the usefulness of the steps in combination as applied to the problem of evaluating the effects of an external stimuli or treatment on cerebral metabolism.

The result of this procedure is to improve the ability to detect changes in a subject's neuronal energy consumption that can be attributed to an external stimuli or treatment. The term "subject" is intended to include patients, normal volunteers, and also non-human mammals such as primates. The procedure does this by reducing the influence on metabolism of extraneous factors (i.e., those factors not specific to the treatment or secondary to the treatment) which would otherwise provide metabolic changes greater than those attributable to the treatment itself. Step 2 (Behavioral control), specifically, minimizes behavioral and subjective influences on metabolism. Step 3 was originally developed for use in PET studies of cerebral blood flow under conditions of sensory or cognitive activation. The merits of this approach in detecting physiological changes compared to the anatomical based methods which are the alternative "state of the art" have been discussed in the literature (Fox, 1991).

Accordingly, the present invention provides a method of evaluating the effects on a subject's brain of administering an external treatment to a subject comprising the following steps:

1. Measuring cerebral metabolism of a subject's brain in the absence of any external treatment administration;
2. Administering an external treatment to the subject;
3. Controlling behavioral influences on the subject's brain by using a behavioral clamp, said behavioral clamp comprising a procedure that:
   (a) Maintains the subject to a standard and stable condition throughout a period of accumulation of cerebral metabolic information with and without said external treatment;
   (b) Is capable of being performed by the subject at comparable levels prior to as well as subsequent to administration of said external treatment;
   (c) Requires a non-stressful level of attention with no opportunity for the subject to develop a productive strategy;
   (d) Includes measurable variables capable of defining desired criteria; and
   (e) Minimizes subjective variables including extraneous ideation, motivation, and anxiety.

4. Measuring cerebral metabolism of the subject's brain after administering the external treatment and during the behavioral clamp; and 5. Determining any differences between cerebral metabolism in the absence of administering the external treatment and cerebral metabolism after administering the external treatment.

The location of metabolic changes which we have noted with this procedure do not necessarily correspond to known locations of receptors for the drugs that we have tested. Instead, they correspond to regions of maximal metabolic change due either to direct or indirect effects of the treatment.

EXAMPLE 1

This study was conducted to determine the effects of oral administration of 40 mg of fluoxetine, an agent which inhibits re-uptake of 5-HT, on CMRglu, as measured by positron emission tomography (PET) using $(^{18}F)$-2-deoxyglucose (FDG) in healthy human subjects.

Materials and Methods

Subjects: Four healthy control subjects were studied. Five potential subjects were screened for personal psychiatric history using the SCID-NP[5] and a clinical mental status examination. They were screened for mental illness with a history and physical examination. Potential subjects were excluded if they had Axis I disorders, substance abuse, alcohol abuse, or significant medical illness, and one was excluded because of a previous episode of major depression. None of the subjects who underwent the full procedures had taken psychotropic medication. Three of the subjects were male and one was female. The age of the subjects range from 20 to 39 years.

Procedures

All PET studies were performed at the Franklin McLean Memorial Research Institute of the University of Chicago using a 3-ring PETT VI scanner. Each subject participated in two PET sessions. Subjects abstained from beverages containing sugar or caffeine and food for at least 4 hours preceding each study. Fluoxetine (40 mg) or matched placebo was administered orally in a double-blind, counter-balanced manner between 11.00 h and 13.00 h. At each session, the subject was positioned in the PETT VI in such a way that slices parallel to the orbital-meatal plane were obtained. A laser beam apparatus and custom-made plastic face mask assured precise and reproducible positioning. A transmission scan was performed in each session for attenuation correction. Intravenous catheters were inserted in each arm for blood sampling and for injection of the radioactive tracer.

Ninety minutes after administration of fluoxetine or placebo, subjects were repositioned in the PET scanner and a visual monitoring task (VMT) was initiated. The task assured a stable behavioral condition at the time of testing. Each subject was asked to press a button with his or her right thumb every time a dim light (50% of trials) was presented on a screen mounted in front of him or her and was asked to ignore every bright light (50%). The lights were presented under computer control at random intervals ranging from 4 to 7 sec. Each subjected completed four blocks of 96 trials each (approximately 10 min per block). Subjects also completed the Profile of Mood States (POMS) before the capsule and 20 min after injection of FDG.

FDG (6.0–7.5 mCi) was administered 30 sec after the initiation of the visual monitoring task and static scanning commenced 40 min later for a period of 14 min. Five simultaneous planes were obtained with an interplane separation of 14 mm. Subjects were then repositioned by moving the subject chair of acquisition of an additional five slices in static mode to more full sample the whole brain. In-plane resolution of PETT VI is 8 mm at full width maximum.

Data Analysis

PET images were reconstructed using standard methods. Slices from the two scanning positions were combined into a single volume for each subject. Average CMRglu was estimated as the mean of all slices, excluding voxels having 60% or less of the maximum metabolic rate (assumed to be ventricles, white matter, and non-brain tissue). Average global CMRglu was compared between placebo and fluoxetine scans using the paired two-tailed t-test.

All voxels were normalized and expressed as a z-score value relative to the whole scan mean and standard deviation of gray matter voxels. PET volumes for each subject were spatially correlated across the two conditions using the surface-fitting technique developed in our laboratory.

PET volumes were also anatomically normalized, i.e., each subject's images were expanded, contracted, rotated, or shifted into a standard volume using the coordinate system of the Talairach atlas, we first identified a set of landmarks which were used to proportionally adjust the entire PET volume into "Talairach space". In Talairach space, the PET slices were linearly interplated between each measured slice to provide better localization of anatomical features.

In the Talairach volumes, two-tailed paired t-tests were performed comparing each voxel from placebo condition to each voxel after fluoxetine. Paired t-tests were used because each subject was tested in each condition. A t-value of 3.2 closely approximated statistical significance for 3 degrees of freedom. To adjust for the large number of voxels studied, we only considered regions significant if a large number of adjacent voxels had t-values greater than 3.2 or less than −3.2. Determination of localization of areas of increased or decreased metabolism were performed by displaying significant voxels in color overlaid on a gray scale MRI.

Results

Average global CMRglu was not significantly different between placebo ($8.93 \pm 0.96$ mg 100 $g^{-1}$ min$^{-1}$) and fluoxetine scans ($8.22 \pm 0.86$ mg 100 $g^{-1}$ min$^{-1}$, paired t=0.82, df3, p<0.48). Inspection of the t-test images revealed that two areas had marked changes in relative glucose metabolism. Most prominent was a bilateral C-shaped region consisting of amygdaloid complex, hippocampal formation, and ventral striatum which showed decreased relative glucose metabolism. A smaller area centered in the right superior parietal lobe (Brodmann area 7) showed increased relative metabolism (FIG. 1).

There were no systematic effects of fluoxetine on reaction time or accuracy on the VMT (median reaction time 571±s.d. 125 ms after placebo, 553±64 msec after fluoxetine, t=−0.78; 91.7±14.6% correct after placebo, 96.4±3.2% correct after fluoxetine, t=0.82). There were no differences in subjective effects as measured by the POMS.

Discussion

FIG. 1 illustrates statistical maps of voxel-by-voxel repeated measures t-tests for the data obtained after subjects had received fluoxetine and placebo. PET images are superimposed on a normal MRI image in Talairach coordinate space, thresholded to show only (values greater than 3.2 (red) or less then −3.2 (blue X)(p<0.05). Red areas show regions in which the fluoxetine condition had greater relative metabolism than placebo; blue areas are regions in which the fluoxetine condition had less relative metabolism than placebo. In each axial slice, the front of the brain is at the top, the left side of the brain is to the left. Each successive slice (from left to right, then top to bottom) shows progressively lower slices in brain, beginning at Talairach coordinates approximately 3.4 cm above AC-PC line; slices are approximately 4.0 mm apart. Sagittal slices begin at the far left of the brain and proceed from left to right, top to bottom in approximately 6.5 mm steps through the midsagittal plane (middle slice in second row) to the far right side. Administration of fluoxetine led to a decrease in CMRglu in bilateral amydeloid complex, hippocampal formation, and ventral striatum and an increase in metabolism centered in the right superior parietal lobe (Brodmann area 7).

EXAMPLE 2

In this study we investigated the brain's response to the psychoactive compound pimozide. Subjects were tested under behavioral conditions substantially identical to the procedures described in Example 1, except pimozide was administered instead of fluoxetine.

Figure 2:
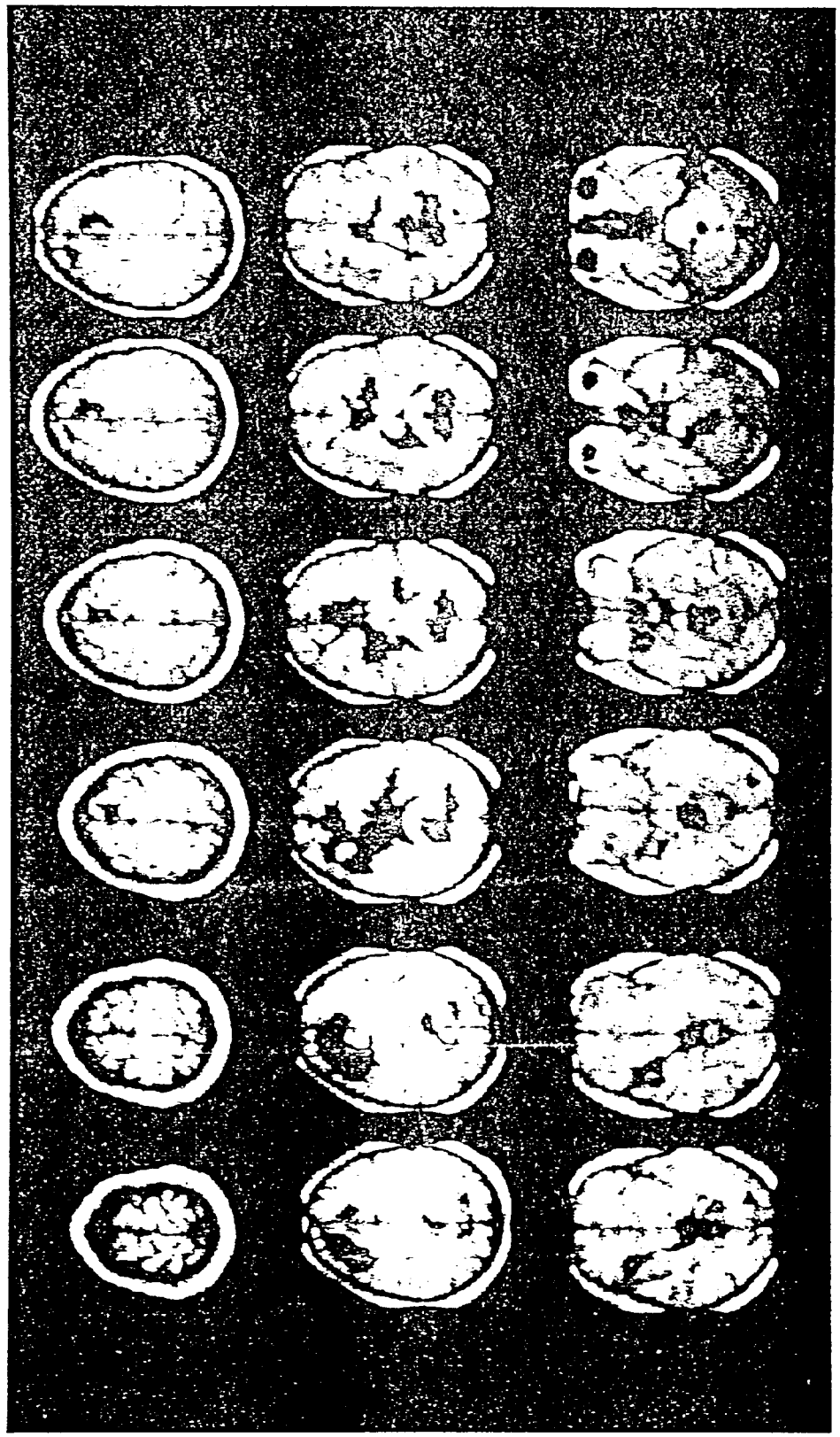
FIG. 2 illustrates a series of PET images superimposed on MRI brain images demonstrating pimizide effects on cerebral glucose metabolism.

FIG. 2 shows changes in rCMglu demonstrating the effects of pimizide

EXAMPLE 3

In the present PET study we tested subjects to investigate individual differences in response to ethanol. Subjects were tested with placebo (tonic water) and with a moderate dose (0.5 g/kg) of ethanol under comparable behavioral conditions substantially in accordance with the procedures described in Example 1.

Figure 3:
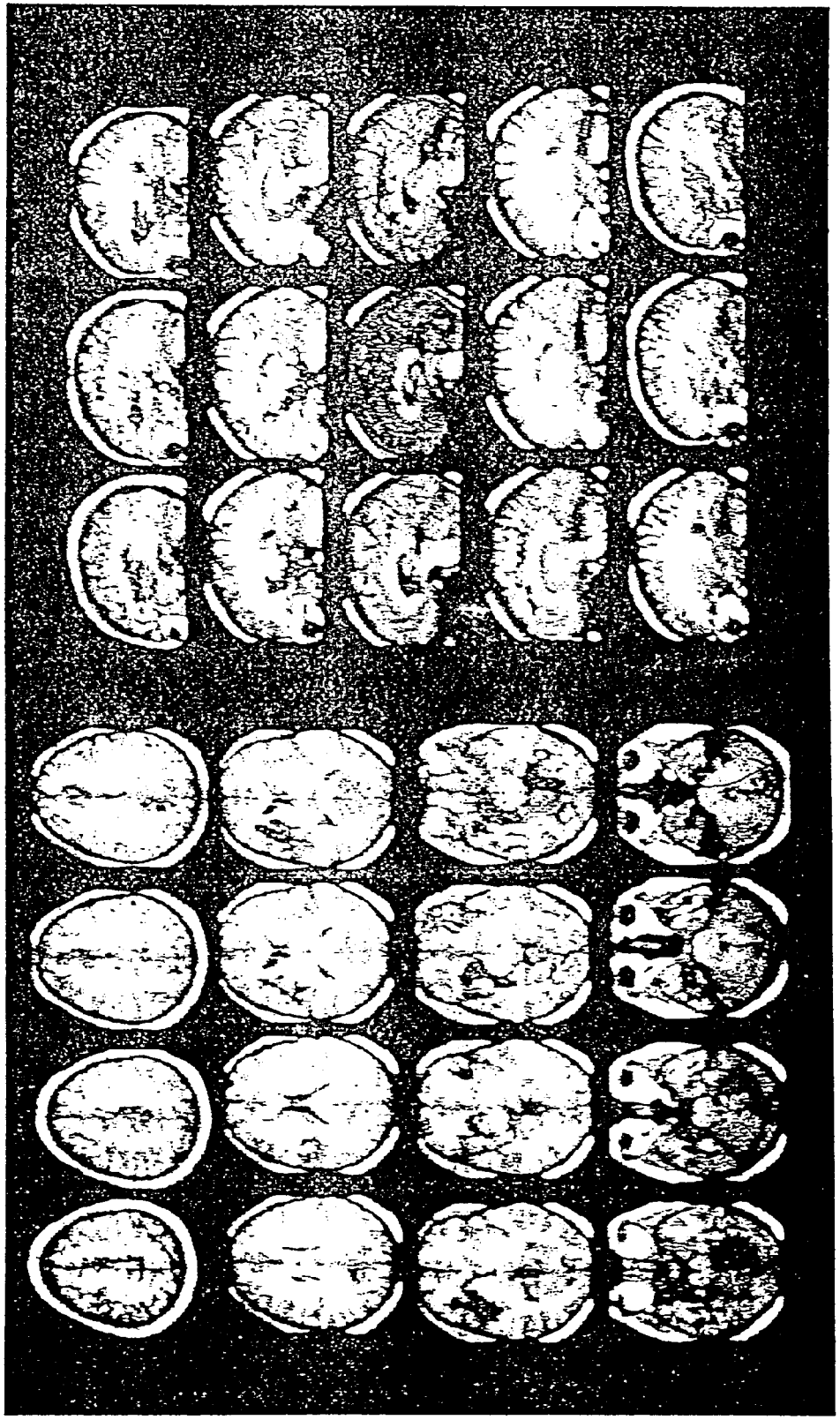
FIG. 3 illustrates a series of PET images superimposed on MRI brain images demonstrating ethanol effects on cerebral glucose metabolism.

FIG. 3 shows changes in rCMglu demonstrating the ethanol effects. The most striking effect was a widespread increase in rCMglu in the left hemisphere. Other areas affected were in the frontal and temporal lobes, basal ganglia, and limbic system.

EXAMPLE 4

In this study we investigated the brain's response to the psychoactive compound nimodipine. Nimodipine (0.5 g/kg) or placebo (mix alone) was administered in a 250 ml beverage in lime juice and tonic water to be consumed in five minutes. All other behavioral conditions were substantially identical to the procedures described in Example 1.

The data appear to show decreased metabolism in the cingulate gyrus and/or left posterior temporal lobe with patchy increased metabolism in the superior portion of the cerebellum and/or interior portion of the occipital lobe.

We claim:

1. A method for determining drug side effects including CNS changes arising from non-brain targeted pharmaceuticals, the method comprising:

(a) using positron emission tomography to measure cerebral metabolism of a patient's or subject's brain prior to any treatment with the non-brain targeted pharmaceutical;

(b) administering the non-brain targeted pharmaceutical to a patient or subject;

(c) controlling behavioral influences on the patient's or subject's brain;

(d) using positron emission tomography to measure cerebral metabolism of the patient's or subject's brain after administering the non-brain targeted pharmaceutical to the patient or subject while controlling behavioral influences on the patient's or subject's brain; and (e) determining any differences between cerebral metabolism prior to administering the non-brain targeted pharmaceutical and cerebral metabolism after administering the non-brain targeted pharmaceutical.

2. The method of claim 1, wherein behavioral influences on the patient's or subject's brain is controlled with a behavioral clamp.

3. The method of claim 2, wherein the behavioral clamp comprised a visual monitoring task (VMT).

4. The method of claim 1, further comprising the step of measuring the patient's or subject's mood both before and after administering the non-brain targeted pharmaceutical.

5. The method of claim 4, wherein the patient's or subject's mood is measuring by administering a standard psychological test to the patient or subject.

6. The method of claim 5, wherein the standard psychological test is a profile of mood states (POMS).

* * * * *